United States Patent [19]

Gruber et al.

[11] Patent Number: 5,082,829
[45] Date of Patent: Jan. 21, 1992

[54] AICA RIBOSIDE PRODRUGS

[75] Inventors: Harry E. Gruber, San Diego; Clinton E. Browne, Oceanside; Bheemaro G. Vgarkar, Escondido; Jack W. Reich, Carlsbad, all of Calif.

[73] Assignee: Gensia Pharmaceuticals, San Diego, Calif.

[21] Appl. No.: 301,222

[22] Filed: Jan. 24, 1989

[51] Int. Cl.$^5$ .............................. A01N 43/; A01N 04; A01N 31/70; C07H 17/02
[52] U.S. Cl. ........................................ 514/43; 536/23
[58] Field of Search ............................. 536/23; 514/43

[56] References Cited

U.S. PATENT DOCUMENTS

| 3,910,885 | 10/1975 | Moffatt | 536/23 |
| 4,575,498 | 3/1986 | Holmes | 536/23 |
| 4,912,092 | 3/1990 | Gruber | 514/45 |

OTHER PUBLICATIONS

CA 83(21): 179457t (1975), J. Org. Chem. 40(20) Srivastava "Nucleosides of 4-Substituted Imidazoles".
CA 86(13): 90175p (1976) Chem. Pharm. Bull. 24(9) Miyoshi "Synthesis of 5-Amino-1-(3'-Deoxy-B-D) .."
CA 109(19): 170789a (1988) Nucleosides Nucleotides 7(3) chambers "Studies in the Protection & Deprotection . . ."

Primary Examiner—Robert A. Wax
Assistant Examiner—Fred Tsung
Attorney, Agent, or Firm—Lyon & Lyon

[57] ABSTRACT

Prodrugs of AICA riboside are provided which increase the bioavailability of AICA riboside and thereby increase extracellular concentrations of the prophylactic and affirmative treatment of various pathologic conditions, including ischemia. Also provided are methods of using AICA riboside prodrugs in treating such conditions.

26 Claims, 3 Drawing Sheets

AICA RIBOSIDE PRODRUGS

FIELD OF THE INVENTION

This invention generally relates to purine nucleosides, specifically to 1-β-D-ribofuranosylimidazole-4-carboxamide ("5-amino-4-imidazolecarboxamide riboside" or "AICA riboside") prodrugs. It also relates to the preparation, use and administration of these compounds which, when introduced into the body, will metabolize into their active forms. This invention also relates to ischemic syndrome treatments, anticonvulsant therapeutic agents, and methods and treatment of seizure and related disorders.

BACKGROUND OF THE INVENTION

The present invention is directed to novel compounds which act as prodrugs of AICA riboside and certain analogs of it. AICA riboside is a naturally occurring intermediate in purine biosynthesis. It is now known to enhance adenosine release from cells during ATP depletion. By virtue of its adenosine releasing abilities, AICA riboside has many therapeutic uses. However, AICA riboside does not cross the blood-brain barrier well and is inefficiently absorbed from the gastrointestinal tract; both characteristics decrease its full potential for use as a therapeutic agent.

Adenosine, 9-β-D-ribofuranosyladenine (the nucleoside of the purine adenine), belongs to the class of biochemicals termed purine nucleosides and is a key biochemical cell regulatory molecule, as described by Fox and Kelly in the *Annual Reviews of Biochemistry*, Vol. 47, p. 635, 1978.

Adenosine interacts with a wide variety of cell types and is responsible for a myriad of biological effects. Adenosine serves a major role in brain as an inhibitory neuromodulator (see Snyder, S. H., *Ann. Rev. Neural Sci.* 8:103-124 1985, Marangos, et al., *NeuroSci and Biobehav. Rev.* 9:421-430 (1985), Dunwiddie, *Int. Rev. Neurobiol.*, 27:63-130 (1985)). This action is mediated by ectocellular receptors (Londos et al., *Regulatory Functions of Adenosine*. pp. 17-32 (Berne et al., ed.) (1983)). Among the documented actions of adenosine on nervous tissue are the inhibition of neural firing (Phillis et al., *Europ. J. Pharmacol.*, 30:125-129 (1975)) and of calcium dependent neurotransmitter release (Dunwiddie, 1985). Behaviorally, adenosine and its metabolically stable analogs have profound anticonvulsant and sedative effects (Dunwiddie et al., *J. Pharmacol. and Exptl. Therapeut.*, 220:70-76 (1982); Radulovacki et al., *J. Pharmacol. Exotl. Thera.*, 228:268-274 (1981)) that are effectively reversed by specific adenosine receptor antagonists. In fact, adenosine has been proposed to serve as a natural anticonvulsant, and agents that alter its extracellular levels are modulators of seizure activity (Dragunow et al., *Epilepsia* 26:480-487 (1985); Lee et al., *Brain Res.*, 21:1650-164 (1984)). In addition, adenosine is a potent vasodilator, an inhibitor of immune cell function, an inhibitor of granulocyte oxygen free radical production, an anti-arrhythmic, and an inhibitory neuromodulator. Considering its broad spectrum of biological activity, considerable effort has been aimed at establishing practical therapeutic uses for adenosine and its analogs.

Sinc adenosine is thought to act at the level of the cell plasma membrane by binding to receptors anchored in the membrane, past work has included attempts to increase extracellular levels of adenosine by administering it into the blood stream. Unfortunately, because adenosine is toxic at concentrations that have to be administered to a patient to maintain an efficacious extracellular therapeutic level, the administration of adenosine alone is of limited therapeutic use. Further, adenosine receptors are subject to negative feedback control following exposure to adenosine, including down-regulation of the receptors.

Other ways of achieving the effect of a high local extracellular level of adenosine exist and have also been studied. They include: a) interference with the uptake of adenosine with reagents that specifically block adenosine transport, as described by Paterson et al., in the *Annals of the New York Academy of Sciences*, Vol. 255, p. 402 (1975); b) prevention of the degradation of adenosine, as described by Carson and Seegmiller in *The Journal of Clinical Investioation*, Vol. 57, p. 274 (1976); and c) the use of analogs of adenosine constructed to bind to adenosine cell plasma membrane receptors.

There are a large repertoire of chemicals that can inhibit the cellular uptake of adenosine. Some do so specifically, and are essentially competitive inhibitors of adenosine uptake, and others inhibit nonspecifically. P-nitrobenzylthioinosine appears to be a competitive inhibitor, while dipyridamole and a variety of other chemicals, including colchicine, phenethylalcohol and papaverine inhibit uptake nonspecifically.

Extracellular levels of adenosine can be increased by the use of chemicals that inhibit enzymatic degradation of adenosine. Previous work has focused on identifying inhibitors of adenosine deaminase, which participates in the conversion of adenosine to inosine. Adenosine deaminase activity is inhibited by coformycin, 2'-deoxycoformycin, and erythro-9-(2-hydroxy-3-nonyl) adenine hydrochloride.

A number of adenosine receptor agonists and antagonists have been generated having structural modifications in the purine ring, alterations in substituent groups attached to the purine ring, and modifications or alterations in the site of attachment of the carbohydrate moiety. Halogenated adenosine derivatives appear to have been promising as agonists or antagonists and, as described by Wolff et al. in the *Journal of Biological Chemistry*, Vol. 252, p. 681, 1977, exert biological effects in experimental systems similar to those caused by adenosine. Derivatives with N-6 or 5'-substitutions have also shown promise.

Although all three techniques discussed above may have advantages over the use of adenosine alone, they have been found to have several disadvantages. The major disadvantages of these techniques are that they rely on chemicals that have adverse side effects, primarily due to the fact that they must be administered in doses that are toxic, and that they affect most cell types nonselectively. As described in *Purine Metabolism in Man*, (eds. De Baryn, Simmonds and Muller), Plenum Press, New York, 1984, most cells in the body carry receptors for adenosine. Consequently the use of techniques that increase adenosine levels 9enerally throughout the body can cause unwanted, dramatic changes in normal cellular physiology. In addition, adenosine deaminase inhibitors prevent the degradation of deoxyadenosine which is a potent immunotoxin. [(Gruber et al. *Ann. New York Acad. Sci.* 451:315-318 (1985)].

It will be appreciated that compounds which increase extracellular levels of adenosine or adenosine analogs at specific times during a pathologic event, without complex side effects, and which would permit increased adenosine levels to be selectively targeted to cells that would benefit most from them, would be of considerable therapeutic use. By way of example, such compounds would be especially useful in the prevention of, or response during, an ischemic event, such as heart attack or stroke, or other event involving an undesired restricted or decreased blood flow, such as atherosclerosis or skin flap surgery, for adenosine is a vasodilator and prevents the production of superoxide radicals by granulocytes. Such compounds would also be useful in the prophylactic or affirmative treatmen of pathologic states involving increased cellular excitation, such as (1) seizures or epilepsy, (2) arrhythmias (3) inflammation due to, for example, arthritis, autoimmune disease, Adult Respiratory Distress Syndrome (ARDS), and granulocyte activation by complement from blood contact with artificial membranes as occurs during dialysis or with heart-lung machines. It would further be useful in the treatment of patients who might have chronic low adenosine such as those suffering from autism, cerebral palsy, insomnia and other neuropsychiatric symptoms, including schizophrenia. The compounds useful in the invention may be used to accomplish these ends.

Compounds which selectively increase extracellular adenosine would also be useful in the prophylactic protection of cells in the hippocampus implicated in memory. The hippocampus has more adenosine and glutamate receptors than any other area of the brain. Accordingly, as described below, it is most sensitive to stroke or any condition of low blood flow to the brain. Some recent studies suggest that Alzheimer's disease may result from chronic subclinical cerebral ischemia. The compounds of the invention, therefore, will be used for the treatment and/or prevention of both overt stroke and Alzheimer's disease.

It is now established that relatively short periods of brain ischemia (on the order of 2 to 8 minutes) set into motion a series of events that lead to an eventual death of selected neuronal populations in brain. This process is called delayed excitotoxicity and it is caused by the ischemia-induced release of the excitatory neurotransmitter glutamate. Within several days post-stroke the neurons in brain are overstimulated by glutamate to the point of metabolic exhaustion and death. Because glutamate appears to be the major factor involved in post-stroke cell damage, the blockade of glutamate receptors in brain could be beneficial in stroke therapy. In animals, glutamate receptor blockers have been shown to be effective in alleviating or reversing stroke associated neural damage. These receptor blockers have, however, been shown to lack specificity and produce many undesirable side effects. Church, et al., "Excitatory Amino Acid Transmission," pp. 115-118 (Alan R. Liss, Inc. 1987).

Adenosine has been shown to be a potent inhibitor of glutamate release in brain. The CA-1 region of brain is selectively sensitive to post-stroke destruction. In studies, where observations were made at one, three and six days post-stroke the CA-1 area was shown to be progressively destroyed over time. However, where cyclohexyladenosine ("CHA"), a global adenosine agonist, was given shortly after the stroke, the CA-1 area was markedly protected. (Marangos et al., Brain Res., in press.) That beneficial effect was also seen in the survival rate of the animals. Because of its global effect, however, CHA has non-specific side effects. For example it undesirably will lower blood pressure and could remove blood from the ischemic area, thereby causing decreased blood flow.

The compounds of the invention described and claimed herein not only show the beneficial adenosine release/glutamate inhibiting properties but are both site and event specific, avoiding the unwanted global action of known adenosine agonists.

Hyperglycemia has been reported to be associated with a poor prognosis for stroke. (Helgason, Stroke 19(8): 1049-1053 (1988). In addition, mild hypoglycemia induced by insulin treatment has been shown to improve survival and morbidity from experimentally induced infarct. (LeMay et al., Stroke 19(11): 1411-1419 (1988)). D-Ribose has been reported to cause hypoglycemia after oral or intravenous administration to experimental animals and humans and Foley (J. Clin. Invest. 37: 719-735 (1958) demonstrated an inhibition of phosphoglucomutase by ribose-5'-phosphate (formed intracellularly after ribose therapy). Although others have suggested that ribose lowers glucose via increased insulin release (Ishiwita et al., Endoncinol. Japan 25: 163-169 (1978)), the preponderance of evidence favors decreased glucose production ove increased utilization. AICA riboside and the prodrugs of the present invention could protect against ischemic injury to the central nervous system (CNS) by their ability to lower blood glucose.

Another area of medical importance is the treatment of neurological diseases or conditions arising from elevated levels of homocysteine (e.g., vitamin B12 deficiencies). The novel AICA riboside prodrugs of this invention may be used for such purposes as well.

A further area of medical importance is the treatment of allergic diseases, which can be accomplished by either preventing mast cell activation, or by interfering with the mediators of allergic responses which are secreted by mast cells. Mast cell activation ca be downregulated by immunotherapy (allergy shots) or by mast cell stabilizers such as cromalyn sodium, corticosteroids and aminophylline. There are also therapeutic agents which interfere with the products of mast cells such as anti-histamines and adrenergic agents. The mechanism of action of mast cell stabilization is not clearly understood. In the case of aminophylline it is possible that it acts as an adenosine receptor antagonist. However, agents such as cromalyn sodium and the corticosteroids are not as well understood.

It will be appreciated, therefore, that effective allergy treatment with compounds which will not show any of the side effects of the above noted compounds, such as drowsiness in the case of the anti-histamines, agitation in the case of adrenergic agents, and Cushing disease symptoms in the case of the corticosteroids would be of great significance and utility. In contrast to compounds useful in the present invention, the AICA riboside prodrugs, none of the three known mast cell stabilizers are known or believed to be metabolized in the cell to purine nucleoside triphosphates or purine nucleoside monophosphates.

Clearly, there is a need for more effective anticonvulsant therapeutic compounds and strategies since most of the currently used antiseizure agents are toxic (e.g., dilantin), or are without efficacy in many patients. Adenosine releasing agents, which enhance adenosine levels during net ATP catabolism will be useful for the treatment of seizure disorders.

A concern in developing adenosine releasing agents, specifically AICA riboside, as anticonvulsants, however, resides in their less than full gastrointestinal tract penetration and their relatively low blood brain-barrier penetration. Derivatization of adenosine releasing agents, including AICA riboside has been undertaken with the goals of increasing penetration of AICA riboside into the brain and through the gut by delivering it as a brain and/or gut permeable form that avoids first pass metabolism and, while reaching the target regenerates into the parent compound (a prodrug strategy).

The present invention is directed to purine prodrugs and analogs which exhibit and, in some cases improve upon, the positive biological effects of AICA riboside and other adenosine releasing compounds without the negative effects of adenosine. The compounds herein defined may be used as prodrugs. The novel compounds typically exhibit one or more of the following improvements over AICA riboside: 1) more potent adenosine releasing effects; 2) increased half-lives; 3) increased brain penetration; 4) increased oral bioavailability; 5) increased myocardial targeting; 6) in some cases synergism with AICA riboside itself.

The AICA riboside prodrugs of this invention may be used in treatment and prevention of a number of disorders, some of which already have been mentioned.

SUMMARY OF THE INVENTION

The present invention is directed to compounds which act as prodrugs of AICA riboside and their use as prodrugs in therapies as described below. These prodrug compounds comprise a modified AICA riboside having an AICA ribosyl moiety and at least one hydrocarbyloxycarbonyl or hydrocarbylcarbonyl moiety per equivalent weight of AICA ribosyl moiety.

It has been found that AICA riboside may be chemically modified to yield an AICA riboside prodrug wherein one or more of the hydroxyl oxygens of the ribosyl moiety (i.e. 2'-, 3'- or 5'-) is substituted with a hydrocarbyloxycarbonyl or hydrocarbylcarbonyl moiety.

These compounds function as prodrugs of AICA riboside and are better absorbed from the gastrointestinal system and are better able to cross the blood-brain barrier than AICA riboside itself. It is believed that the modifying ester side groups allow for improved capabilities in absorption from the gastrointestinal system and in reduced first pass metabolism, as well as in making more drug available for crossing the blood-brain barrier. As the prodrug molecule approaches or reaches the active site, intact modifying groups can be endogenously cleaved to regenerate AICA riboside.

The prodrug compounds of the present invention are useful in treating a variety of clinical conditions where increasing extracellular levels and release of adenosine would be beneficial. Accordingly, the present invention is directed to the prophylactic and affirmative treatment of such conditions as stroke, Alzheimer's disease, homocysteineuria, skin flap and reconstructive surgery, post-ischemic syndrome and other seizure-related conditions, and myocardial ischemia, using these prodrug compounds. This invention is also directed to pharmaceutical compositions comprising an effective amount of a prodrug compound of the present invention in a pharmaceutically acceptable carrier.

In one aspect, the present invention is directed to novel prodrug compounds which comprise a modified AICA riboside having a AICA ribosyl moiety and at least one hydrocarbyloxycarbonyl or hydrocarbylcarbonyl moiety, or combinations thereof, per equivalent weight of AICA ribosyl moiety, provided that said prodrug does not have two or more of the same hydrocarbylcarbonyl moieties per equivalent weight of AICA ribosyl moiety. Preferred prodrug compounds include those where at least one of the hydroxyl oxygens of the ribosyl moiety is substituted with a hydrocarbyloxycarbonyl or hydrocarbylcarbonyl moiety. Particularly preferred are compounds wherein at least one hydroxyl oxygen is substituted with a hydrocarbyloxycarbonyl moiety. One preferred class of prodrug compounds comprises compounds wherein either the 3'- or 5'-hydroxy oxygen of the ribosyl moiety is substituted with a hydrocarbyloxycarbonyl moiety.

Definitions

As used herein, the following terms have the following meanings, unless expressly stated to the contrary:

The term "alkyl" refers to saturated aliphatic groups, including straight, branched and carbocyclic groups.

The term "alkenyl" refers to unsaturated alkyl groups having at least one double bond [e.g. $CH_3CH=CH(CH_2)_2-$] and includes both straight and branched-chain alkenyl groups.

The term "alkynyl" refers to unsaturated groups having at least one triple bond [e.g. $CH_3C\equiv C(CH_2)_2-$] and includes both straight chain and branched-chain groups.

The term "aryl" refers to aromatic hydrocarbyl and heteroaromatic groups which have at least one aromatic ring.

The term "alkylene" refers to straight and branched-chain alkylene groups which are biradicals, and includes, for example, groups such as ethylene, propylene, 2-methylpropylene

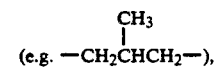

(e.g. $-CH_2CHCH_2-$),

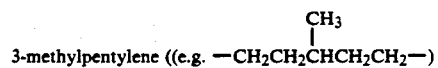

3-methylpentylene ((e.g. $-CH_2CH_2CHCH_2CH_2-$)

and the like.

The term "hydrocarbyl" denotes an organic radical composed of carbon and hydrogen which may be aliphatic (including alkyl, alkenyl, and alkynyl groups and groups which have a mixture of saturated and unsaturated bonds), alicyclic (carbocyclic), aryl (aromatic) or combinations thereof; and may refer to straight-chained, branched-chain, or cyclic structures or to radicals having a combination thereof, as well as to radicals substituted with halogen atom(s) or heteroatoms, such as nitrogen, oxygen, and sulfur and their functional groups (such as amino, alkoxy, aryloxy, lactone groups, and the like), which are commonly found in organic compounds and radicals.

The term "hydrocarbyloxycarbonyl" refers to the group

wherein R' is a hydrocarbyl groups.

The term "hydrocarbylcarbonyl" refers to the group

wherein R' is a hydrocarbyl group.

The term "ester" refers to a group having a

linkage, and includes both acyl ester groups and carbonate ester groups.

The term "halo" or "halogen" refers to fluorine, chlorine, bromine and iodine.

The term "carbonate ester" refers to the group

wherein R' is hydrocarbyl or to compounds having at least one such group.

The term "acyl ester" refers to the group

wherein R' is hydrocarbyl or to compounds having at least one such group.

The term "mixed ester" refers to compounds having at least one carbonate ester group and at least one acyl ester group.

In referring to AICA riboside the prodrugs of the present invention, the following conventional numbering system for the rings is used:

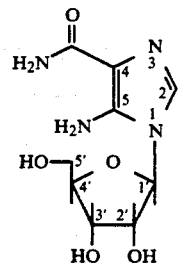

DETAILED DESCRIPTION OF THE INVENTION

Preferred Prodrug Compounds

Figure 1:
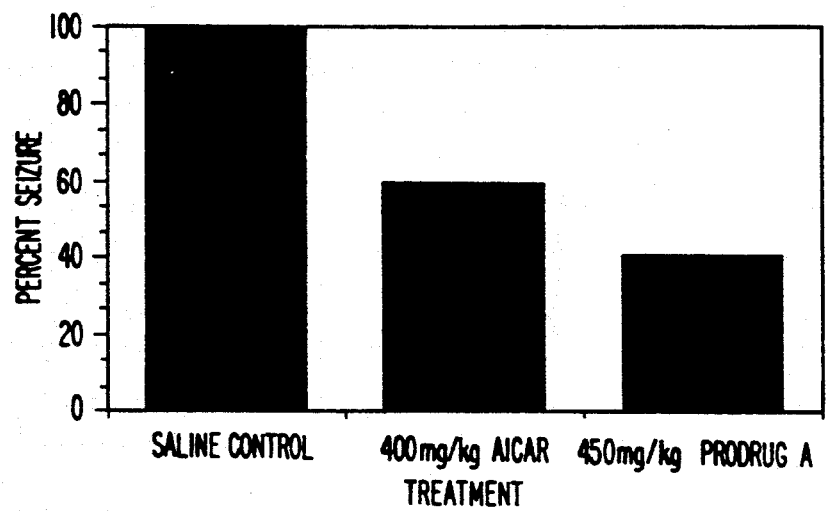
FIG. 1 depicts the activities of AICA riboside and Prodrug A in preventing homocysteine thiolactone-induced seizures in mice.

Preferred prodrug compounds of the present invention include those having the following formula:

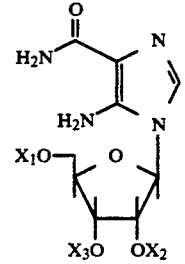

(I)

wherein $X_1$, $X_2$, and $X_3$ are independently hydrogen,

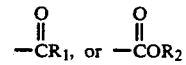

wherein $R_1$ and $R_2$ are independently hydrocarbyl preferably of from 1 to about 24 carbon atoms, or two of $X_1$, $X_2$ and $X_3$ taken together form a cyclic carbonate group, with the proviso that not all of $X_1$, $X_2$ and $X_3$ are hydrogen, acetyl, or propionyl or benzoyl or if one $X_1$, $X_2$ and $X_3$ is hydrogen, the other two are not both benzoyl. Preferred $R_1$ and $R_2$ groups include lower alkyl groups, especially preferred are those having at least one secondary carbon atom. Hydrocarbyl groups having more than 24 carbon atoms may be used and are considered to be within the scope of the present invention.

Preferred compounds include those having one or two ester groups. More preferred are those having one ester group. Especially preferred are compounds having an ester group at either the 3'- or 5'- position of the ribosyl ring.

One preferred class of compounds is the carbonate esters.

Particularly preferred are compounds wherein $X_1$ and $X_3$ is

especially preferred are such compounds where $X_2$ is hydrogen.

In one especially preferred compound, $X_1$ and $X_2$ are hydrogen and $X_3$ is isobutoxycarbonyl.

Preparation of Preferred Compounds

The preferred carbonate ester and acyl ester compounds of the present invention may be conveniently prepared according to the following reaction scheme:

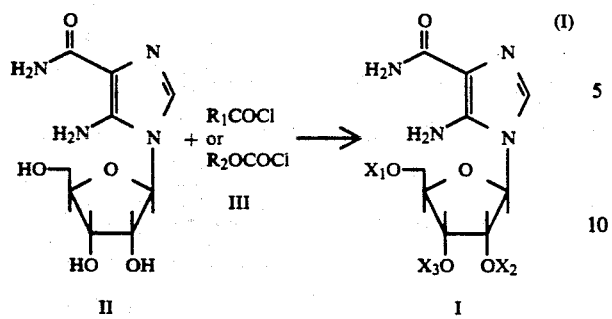

wherein $X_1$, $X_2$, $X_3$, $R_1$, and $R_2$, are as defined in conjunction with formula (I).

Reaction (1) is carried out by combining II, AICA riboside, and III, the appropriate acid chloride or chloroformate, in solvents. The acid chloride may be conveniently prepared by conventional procedures such as reaction of the corresponding acid with thionyl chloride; some acid chlorides are commercially available. Many chloroformates are commercially available; also, the cloroformates may be conveniently prepared by conventional procedures known to those skilled in the art by the reaction of phosgene with the appropriate alcohol. Reaction (1) is conducted at a temperature of from about $-10°$ C. to about $5°$ C., preferably from about $-5°$ C. to about $0°$ C. and is generally complete within about 2 to about 4 hours. For ease of handling, the reaction is carried out in solvents. Suitable solvents include dimethylformamide (DMF), pyridine, methylene chloride and the like. For convenience, the reaction is carried out at ambient pressure. The reaction product(s) are isolated by conventional procedures as column chromatography, cyrstallization and the like. As may be appreciated, the reaction may result in a mixture of products, mono, di, and tri-ester at the 2'- 3'- and/or 5'- positions of the ribosyl moiety. The product esters may be separated by conventional procedures such as thin layer chromatography (TLC), high pressure liquid chromatography (HPLC), column chromatography, crystallization, and the like which are well known to those skilled in the art.

The 5'-monoesters may be conveniently prepared according to the following reaction scheme to give an intermediate blocked at the 2' and 3' positions:

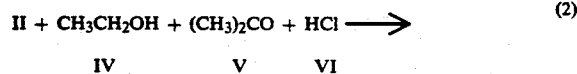

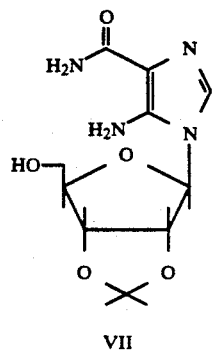

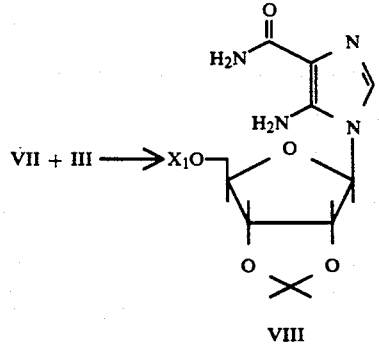

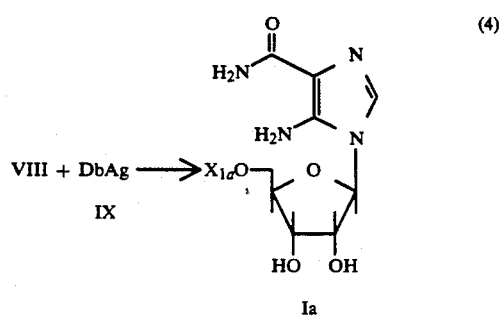

wherein $X_{1a}$ is

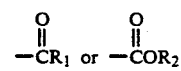

and DbAg is a deblocking agent.

Reaction (2) is conducted by combining II, IV, V and VI. Although the reactants may be combined in any order, it may be preferred to add II to a mixture of IV, V and VI. The reaction is carried out at a temperature of about $10°$ C. to about $25°$ C., preferably from about $15°$ C. to about $25°$ C. and is generally complete within about 5 hours. Intermediate VI is isolated by conventional procedures.

Reaction (3) is the reaction of intermediate VII with the appropriate acid chloride or chloroformate and is carried out as described in connection with Reaction (1).

Reaction (4) is an optional step to remove, if desired, the cyclic blocking group from the 2' and 3' positions. It is carried out be reacting with IX, the appropriate deblocking agent. Suitable deblocking agents include H+ resin in water/acetone, tetraethyl-ammonium fluoride/THF, acetic acid/water, and the like. Such deblocking reactions are conventional and well known to those skilled in the art.

Mixed ester compounds may be conveniently prepared by first reacting AICA riboside with the appropriate acid chloride according to Reaction (1) to add the acyl ester group and then reacting the acyl ester-substituted compound with the appropriate chloroformate according to Reaction (1) to obtain the mixed ester.

Utility

As noted previously, the prodrug compounds of the present invention are useful in treating a variety of clinical conditions where increased extracellular levels (and/or release) of adenosine are beneficial.

In particular, these compounds are useful in stroke therapy, either by prophylactic treatment or by treatment soon after the cerebral vascular event. These compounds are useful in mitigating the effects of post-ischemic syndrome in the central nervous sytem, including the brain and spinal chord.

It is now clear that relatively short periods of brain ischemia set into motion a series of events that lead to an eventual death of selected neural populations in brain caused by the ischemia induced overproduction of the excitatory neurotransmitter glutamate. Thrombolytic therapy of stroke is therefore not sufficient to protect against the ensuing neurologic damage after the occlusion is removed.

Since glutamate appears to be the major factor involved in post-stroke cell damage it is reasonable to expect that blockade of glutamate release in brain with adenosine might be beneficial in stroke therapy. Known glutamate receptor blockers have however been shown to lack specificity and produce many undesirable side effects, and the undesirable affects of adenosine administration have been noted. However, low doses of adenosine or an adenosine agonist with a high $A_1$ to $A_2$ affinity might avoid cardiovascular side effects and bind the $A_1$ receptors in the hippocampal regions thereby preventing or reducing g utamate release.

AICA-riboside has been shown to protect against cellular degeneration that results after experimentally induced brain ischemia in two different animal model systems. In a gerbil model employing 5 minutes of global ischemia followed by reperfusion, AICA-riboside prevented the degeneration of hippocampal CA-1 cells, which in the control animals (non AICA-riboside treated) were virtually completely destroyed. Both intracerebroventricular (ICV) and IP administration of AICA riboside was effective in the gerbil model. In addition to the gerbil, two different rat models of focal ischemia were also used to evaluate AICA-riboside. One model employed partial reperfusion and the second total reperfusion. Both protocols showed a highly significant reduction in infarct size when a 800 mg/kg dose of AICA-riboside was given IP.

These compounds are also useful in treating other ischemic conditions, particularly those involving myocardial ischemia such as heart attacks and angina pectoris.

During a heart attack, adenosine is normally released and assists in maintaining the patency of ischemic vessels through vasodilation and inhibition of granulocyte free radical production and concomitant microvascular plugging, as described below. The prodrug compounds of the present invention enhance adenosine release and, therefore enhance the normal protective effect of adenosine during such an ischemic event. Normally, during such an event the production of inosine is greater than that of adenosine. In an area of low flow during coronary occlusion, the ratio of inosine to adenosine may be approximately 4 to 1 in ischemic tissue. A certain percentage of inosine and adenosine subsequently exit the cell and are present in the immediate extracellular environment. The compounds of the present invention enhance the ischemic tissue ratio of adenosine to inosine. Adenosine levels are not altered significantly throughout the patient because alterations of adenosine production only occur in areas of, and at the time of, net ATP use and because adenosine is rapidly degraded. Thus, there will be a localized increased level of extracellular adenosine instead of a systemic or generalized adenosine enhancement.

Since many of the damaging events during ischemia occur rapidly, the prodrugs of the present invention should be present at the earliest possible moment. Accordingly, prophylactic use of these prodrugs may slow or interrupt the damaging process early enough to prevent any permanent damage. For example, the increased microvascular blood flow from vasodilation and decreased white cell sticking could maintain microvascular potency as well as in a sense wash away clots, clot promoting matter, or other deleterious agents from the proximal atherosclerotic regions.

In addition, since the prodrugs of the present invention when taken prophylactically would enhance adenosine release during an ischemic event, a heart attack patient undergoing such treatment would have a greater chance of not dying of a sudden arrhythmia before entry to the hospital. Such a prophylactic therapeutic regimen would protect the microvascular system and allow a longer time frame in which to institute thrombolytic therapy.

Moreover, the prodrugs of the present invention will also be useful in combination with thrombolytic agents such tissue plasminogen activator, streptokinase, and the like and also with other agents which are either free radical scavengers or agents which prevent the production of free radicals.

The prodrugs of the present invention are useful in treating reduced blood flow caused by myocardial arrhythmia. Prophylactic treatment with AICA riboside has been shown to result in decreased numbers of premature ventricular depolarizations and ventricular tachycardia episodes in animals and, more recently, decreased fatal ventricular fibrillation.

In addition AICA riboside has now been demonstrated to cause hypoglycemia in rats, rabbits, dogs and man. This effect may contribute to the anti-ischemic properties of the molecule and suggests that means of increasing intracellular ribose such as treatment with ribose itself or inosine, guanosine, adenosine, thymidine, uridine and cytosine (i.e. nucleosides) and prodrugs and analogs of them which can be cleaved to yield ribose-1-phosphate (which is converted ribose-5-phosphate) or ribose-5-phosphate may also protect against ischemic injury to the central nervous system. Furthermore, AICA riboside has now been shown to be generated from ZMP during ischemia. The localized dephosphorylation of ZMP in an ischemic region results in selectively high concentrations of AICA riboside and, therefore, ischemic selective effects of the molecule. For example, adenosine deaminase (ADA) would be only slightly inhibited by a dose of up to 500 mg/kg AICA riboside, but during tissue ischemia, the localized built up of AICA riboside should cause significant inhibition of ADA. This ischemia-specific effect would avoid the deleterious effects of systemic ADA inhibition.

In addition, the prodrugs of the present invention may be useful in treating other conditions in which administration of AICA riboside has been beneficial. Such as treatment of autoimmune and inflammatory diseases, conditions potentially associated with chronically low adenosine (including autism, insomnia, cerebral palsy, schizophrenia and other neuropsychiatric conditions), and allergic conditions (especially by preventing the release of pharmacologically active substances by mast cells).

However, as previously noted, AICA riboside is inefficiently absorbed from the gut and is poor in crossing the blood-brain barrier to penetrate the affected foci in the brain.

The advantageous features of more efficient absorption from the GI tract and better crossing of the blood brain barrier of the prodrug compounds of the present invention should give them increased efficacity and improved therapeutic effect as compared to AICA-riboside itself.

In addition the prodrug compounds of the present invention are useful as anticonvulsants and in preventing seizures in individuals with epilepsy including patients with homocysteineuria.

Both AIC riboside and some of these prodrug compounds have been shown to be active in preventing homocysteine-induced seizures in laboratory animals.

In addition AICA riboside and the prodrugs of the present invention should be efficacious in reducing ischemic injury to the CNS The enhanced localized adenosine should cause local vasodilation, decreased granulocyte activation and trapping, and decreased glutamate release and excitatory neurotoxicity. The mild hypoglycemia resulting from administration of these compounds is also protective.

Description of Preferred Embodiments

We have recently identified a series of prodrugs of AICA riboside having advantageous therapeutic properties. The structures of these prodrug compounds are depicted in Table I. These prodrug compounds exhibit better penetration of the blood-brain barrier in comparison with AICA riboside itself as shown by their activities in inhibiting homocysteine thiolactone ("HTL") induced seizures.

A prodrug of AICA riboside with the assigned structure: 3'-isobutoxycarbonyl-AICA riboside which appears as Compound 1 of Table 1 ("5-amino-3'-(2-methyl-1-propoxycarbonyl)-1-$\beta$-D-ribofuranosyl-imidazole-4-carboxamide" or "Prodrug A") has been found to be particularly good for prolonging the half-life of AICA riboside and in penetrating the gut barrier. It has improved anticonvulsant activity against HTL-induced seizures when compared to AICA riboside. Prodrug A is approximately 30% more potent than AICA riboside on a molar basis (FIG. 1).

Figure 2:
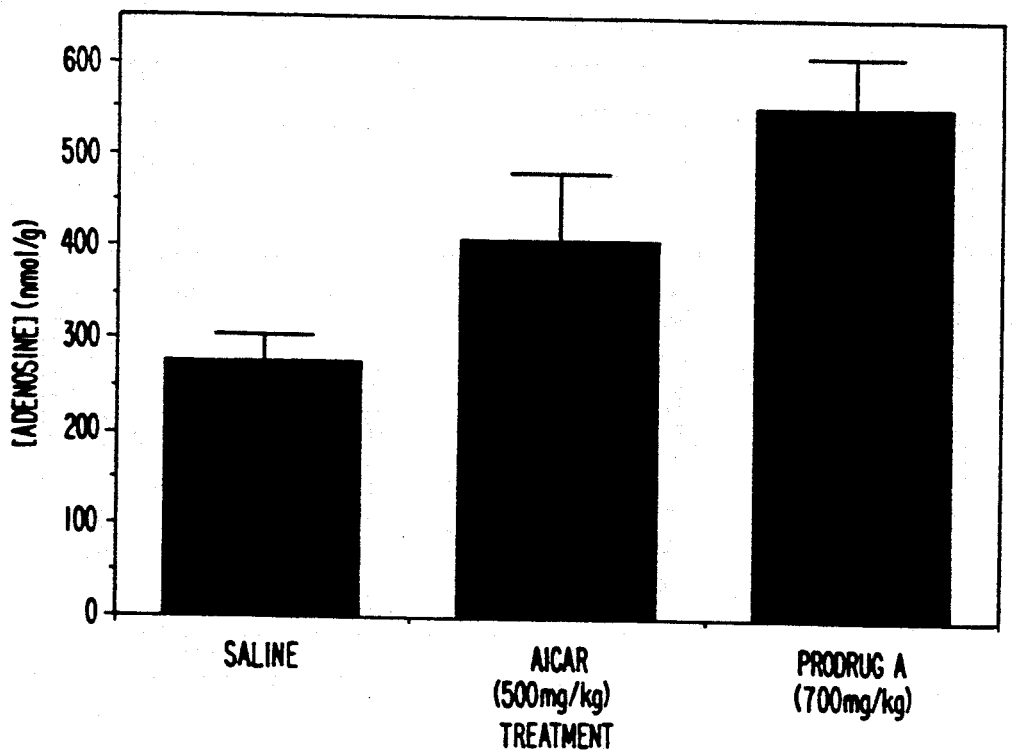
FIG. 2 depicts the activities of AICA riboside and Prodrug A in inducing adenosine production in ischemic rat heart tissue.

The ability of this compound to enhance adenosine production in an ischemic heart model has also been demonstrated (FIG. 2). Prodrug A was about 30% more potent on a molar basis than AICA riboside. The detection of substantial phosphorylated derivative of AIC riboside (ZMP) following administration of this compound further demonstrated that Prodrug A analog was in fact being cleaved to AICA riboside because that cleavage is necessary for the intracellular phosphorylation of AICA riboside to ZMP to occur. Surprisingly, Prodrug A also led to less AICA riboside and, therefore, less ZMP accumulation in the heart than an equimolar dose of AICA riboside and yet had more adenosine production indicating it may have analog activity.

In summary, 3'-isobutoxycarbonyl - AICA riboside has demonstrated improved enhancement of adenosine production as compared with the AICA riboside itself. It has an increased half-life as evidenced by the fact that it is cleared and phosphorylated more slowly than AICA riboside. Also, the maximum therapeutic effect of the compound appears to be greater than AICA riboside on a molar basis. This compound, furthermore, exhibits anti-seizure activity in the homocysteine-induced seizure model and increases adenosine production in the myocardial ischemia model. This compound also crosses the gut better that AICA riboside, as there is 5 times more ZMP accumulation in the liver after an equimolar gavage, and has reduced first pass metabolism.

To assist in understanding the present invention, the following examples follow, which include the results of a series of experiments. The following examples relating to this invention should not, of course, be construed in specifically limiting the invention, and such variations of the invention, now known or later developed, which would be within the perview of one skilled in the art are to be considered to fall within the scope of the present invention hereinafter claimed.

EXAMPLE 1

Preparation of Carbonate Esters of AICA Riboside

Carbonate esters of AICA riboside are prepared according to the following procedure:

A 70 mmol portion of AICA riboside is suspended in a mixture of 50 ml N, N-dimethylformamide and 50 ml pyridine and then cooled in an ice-salt bath. To the resulting mixture the appropriate chloroformate (94 mmol, a 20 percent excess) is added under anhydrous conditions over a period of about 15 to 30 minutes with constant stirring. The salt bath is removed. The reaction mixture is allowed to warm to room temperature over about 1 to 2 hours. The progress of the reaction is monitored by TLC on silica gel, eluting with 6:1 methylene chloride:methanol. Disappearance of AICA riboside indicates completion of the reaction. The solvents are removed by evaporation under high vacuum (bath temperature less than 40° C.). The residue is chromatographed on a silica gel column packed with methylene chloride and is eluted initially with methylene chloride and then with methylene chloride: methanol 95:5. Fractions showing identical (TLC) patterns are pooled and then the eluate is evaporated to give a foam. The foam is dried overnight under high vacuum at room temperature.

The yield of the product carbonate esters is about 45 to 65%. Although the primary product is the 5'-carbonate ester, other product esters are prepared.

EXAMPLE 2

Preparation of 3'-Isobutoxycarbonyl AICA Riboside

A solution of AICA riboside (18.06 g, 70 mmol) in a mixture of pyridine (50 ml) and N,N-dimethylformamide (50 ml) was cooled in an ice-salt mixture. To it was added an isobutyl chloroformate (11.47. g, 94 mmol) slowly over a period of 30 minutes with constant stirring. The initial red color of the reaction turned pale yellow in about 40 minutes. Stirring was continued for 2 hours at the end of which TLC on silica gel, eluting with methylene chloride: methanol 9:1 (Rf=0.3), indicated completion of the reaction. Methanol (2 ml) was added to neutralize unreacted reagents. The solvents from the reaction mixture were removed by evaporation under high vacuum (bath temperature approximately 40° C.). The sticky mass remaining was chromatographed over a silica gel column packed in a 9:1 methylene chloride: methanol mixture. The column was eluted with the same mixture and several fractions were collected. Fractions showing identical TLC spots were pooled and evaporated to obtain an off-white foam. The product isolated from the foam had the assigned structure, based on the nmr spectrum: 3'-isobutyloxycarbonyl-AICA riboside. Yield 8.5 g; mp 71°-73° (not a sharp mp) IR (nujol) 1725 cm-1 (—OCO$_2$CH$_2$CH(CH$_3$)$_2$), nmr(DMSO-d$_6$), δ ppm, 0.9 [d, 6H (CH$_3$)$_2$], 1.9 (m, 1H, CH of isobutyl side chain), 3.6 (m, 2H, 5'—CH$_2$), 3.9 (d, 2H, CH$_2$ of isobutyl side chain), 4.1(m, 1H, 4'—CH), 4.6(1, 1H, 2'—CH), 5.01(dd, 1H, 3'—CH), 5.45–5.55(m, 2H, 1'—CH and 5'—OH), 5.92(d, 1H, 2—OH), 6.02(br.s, 2H, 5—NH$_2$), 6.6–6.9(br. d, 2H, 4—CONH$_2$), 7.35 (S, 1H, 2—CH).

The spectra of this compound was compared with that of its parent compound, AICA riboside and showed that 3-CH (which appears at 4.05 ppm in AICA riboside), had shifted down field by 1 ppm due to a substitution on the oxygen attached to the same carbon atom, while the positions of all the other protons remained unchanged for the most part, thus confirming the substitution to be on 3'-C.

Although nmr of the product of Example 2 indicated that it was at least 80% of the 3'-isobutoxycarbonate ester (Compound 1 of Table I), HPLC analysis showed several peaks. The fractions corresponding to each peak were collected and analyzed on HPLC. Each peak also showed the presence of two major products, designated A and B. One of them (product A) was determined to be AICA riboside and the other (product B) was isolated in small quantities and characterized as AICA riboside-2', 3'-cyclic carbonate based on its nmr and mass spectral data. nmr(DMSO-d$_6$) δ ppm, 3.6–3.7(m, 2H, 5'—CH$_2$), 4.3 (q, 1H, 4'—CH), 5.35 (m, 1H, 3'—CH), 5.6 (m, 1H, 2'—CH), 5.2–6.7 (br, 1H, 5'—OH), 5.8–6.0 (br, 2H, 5—NH$_2$), 6.1 (d, 1H, 1'—CH), 6.7–6.95(br, d, 2H, 4—CONH$_2$), 7.45 (S, 1H, 2—CH). Mass spec, (FAB) M+, 284; M$^{+1}$ 285, M$^{+2}$ 286. These data confirmed the structure of the compound (product B) to be 2'3'-cyclic carbonate of AICA riboside. A preferred method of synthesis of this compound is set forth in Example 3 below.

EXAMPLE 3

Preparation of AICA Riboside 2', 3'-Cyclic Carbonate

To a suspension of AICA-riboside (5.16 g, 20 mmol) in pyridine (50 ml), p-nitrophenyl chloroformate 92.5 g, 25 mmol) was added in one lot and stirred at room temperature for 5 days at the end of which TLC on silica gel, eluting with methylene chloride: methanol, (6:1 Rf=0.4), indicated completion of the reaction. Pyridine from the reaction mixture was removed by evaporation. The residue was chromatographed over a silica gel column, eluting with methylene chloride:methanol (9:1). The fractions which showed identical TLC were pooled and evaporated to obtain a foam (yield, 4.0 g). This product was identical to AICA riboside-2',3'-cyclic carbonate, isolated as one of the by-products from the synthesis described in Example 2 and characterized by nmr and mass spectral analysis.

EXAMPLE 4

Preparation of 5'-Acetyl AICA Riboside

To a mixture of dry HCl gas (9.0 g) dissolved in dry acetone (115 ml) and absolute ethanol (138 ml), AICA-riboside (12.9 g), was added. The mixture was stirred at room temperature for two hours. Completion of the reaction was monitored by TLC. The reaction mixture was stirred an additional two hours at room temperature at which time TLC indicated that the reaction was complete. The reaction mixture was poured slowly into an ice-cold mixture of ammonium hydroxide (18 ml) and water (168 ml). The pH of the solution was adjusted to about 8 by adding a few ml of ammonium hydroxide. The reaction was concentrated to 100 ml. The ammonium chloride precipitate was removed by filtration. The filtrate was concentrated again to precipitate additional ammonium chloride. After filtering, the filtrate was evaporated to dryness. The residue was extracted three times with 200 ml aliquots of methylene chloride. Evaporation of methylene chloride gave a foam which was characterized by nmr spectroscopy to be the products 2',3'-isopropylidene AICA riboside which was used in the following reaction without further purification.

To a solution of 2',3'-isopropylidene AICA riboside in 25 ml dry pyridine cooled in an ice-salt mixture, 10 ml acetic anhydride was added dropwise with stirring; the mixture was warmed to room temperature over a period of two hours. The reaction was shown to be complete by TLC (9:1 methylene chloride: methanol). The solvents were removed from the reaction mixture by evaporation. The residue was coevaporated twice with two 25 ml aliquots of N, N-dimethylformamide. That product was treated with 100 ml of 80% acetic acid for twenty-four hours. Completion of the reaction was indicaated by TLC on silica gel eluting with 6:1 methylene chloride:methanol. Water and acetic acid were removed by evaporation under reduced pressure. The residue was coevaporated four times with 100 ml aliquots of water to remove the acetic acid. The residue was crystallized from 25 ml 1:1 ethanol:water. The crystalline product was collected by filtration, washed with water and dried under vacuum to give 3.0 g of the above-identified product, melting point 165°–166° C. IR(nujol), 1745 cm$^{-1}$ (—OCOCH$_3$); nmr (DMSO-d$_6$), δ ppm 2.0 (S,3H, COCH$_3$), 4.0–4.1 (m, 2H, 5'—CH$_2$), 4.1–4.4 (m, 3H, 2'—CH, 3'—CH, 4'—CH), 5.3 (d, 1H, 1'—CH), 5.4–5.6 (m, 2H, 3'—OH, 4'—OH), 5.7–5.9 (br, 2H, 5—NH$_2$), 6.6–7.0 (br. d, 2H, CONHz), 7.3 (S, 1H, 2—CH).

By using the following procedures described in Examples 1 to and in the Detailed Description of the Invention, the compounds listed in Table I were prepared. Also, by using the following procedures described in Examples 1 to 4 and in the Detailed Description of the Invention, the compounds listed in Tables II and III are prepared.

EXAMPLE A

Activity in Inhibiting HTL Included Seizures

Compounds were tested for their activities in inhibiting HTL induced seizures in rats.

Animals used were male Swiss Webster mice weighing 21–30 grams (Charles River Breeding Labs, Wilimington, MA). All animals were adapted to the laboratory for at least 5 days prior to use.

All solutions to be injected were prepared as a single injection cocktail at a concentration such that 1 ml per 100 g of body weight yielded the desired dose. The solutions were compounded as follows: Homocysteine Thiolactone - HCl (HTL-HCl) (Sigma Chemical Company, St. Louis, MO) was dissolved in distilled water and the pH adjusted to 6.7 with NaOH. Pentylenetetrazol (PTZ) was dissolved in 0.9% saline. Prodrug compounds or AICA riboside (Sigma) when used alone was dissolved in distilled water. All solutions containing Mioflazine (Janssen Pharmaceuticals) were prepared at a final DMSO concentration of 10–15% as were the Dipyridamole (Sigma) solutions. N-ethylcarboxamide adenosine, NECA (Sigma) and Flunitrazepam (Hoffman La Roche) injections were prepared in a final ethanol concentration of 0.2%. In all cases carrier control solutions of carrier were injected that were matched for both tonicity and solvents to the test solutions. All test and control solutions were injected via a bolus, I.P., using a 27 gauge needle. HTL and PTZ were injected subcutaneously in the upper back of the animal.

Animals were preinjected with either control solution containing only carrier or test solution containing candidate compound (prodrug or AICA riboside) and carrier in groups of 6-8 per test solution or control. The seizure inducing composition solution was injected at a specific time interval thereafter (ranging from 15 minutes to several hours, most experiments utilized a 30 minute interval). After injection of the seizure inducing composition animals were isolated in separate cages and observed for the onset of a seizure. In most experiments animals were scored as being fully protected from a seizure if they failed to seize for a period 2-3 hours following homocysteine thiolactone (HTL) injections (carrier control latency about 20 minutes) and 1 hour after PTZ administration (carrier control seizure latency of 4 minutes). Seizures noted were either clonic or clonic-tonic in nature and varied in severity from forelimb clonus to full tonic extension of hind limbs and forelimbs. In all experiments the seizure latency was also noted as was the mortality rate in animals having seizures. The overt character of both the PTZ and HTL seizures were quite similar, although the latency of the former was markedly shorter.

Results of testing one of the compounds of the present invention, 3'-isobutoxycarbonyl AICA riboside (Prodrug A, Compound 1 of Table I), and AICA riboside for prevention of HTL induced seizures are shown in FIG. 1.

EXAMPLE B

Adenosine, AICA Riboside and ZMP Levels in Ischemic Heart Tissue

Prodrug compounds of the present invention and AICA riboside were tested for their activity in enhancing the production of adenosine and increasing production of AICA riboside from ZMP in ischemic heart tissue in rats.

Samples of heart tissue after ischemia were analyzed for nucleoside and nucleotide levels. Samples were measured for adenosine, AICA riboside and ZMP concentrations by HPLC.

Figure 3:
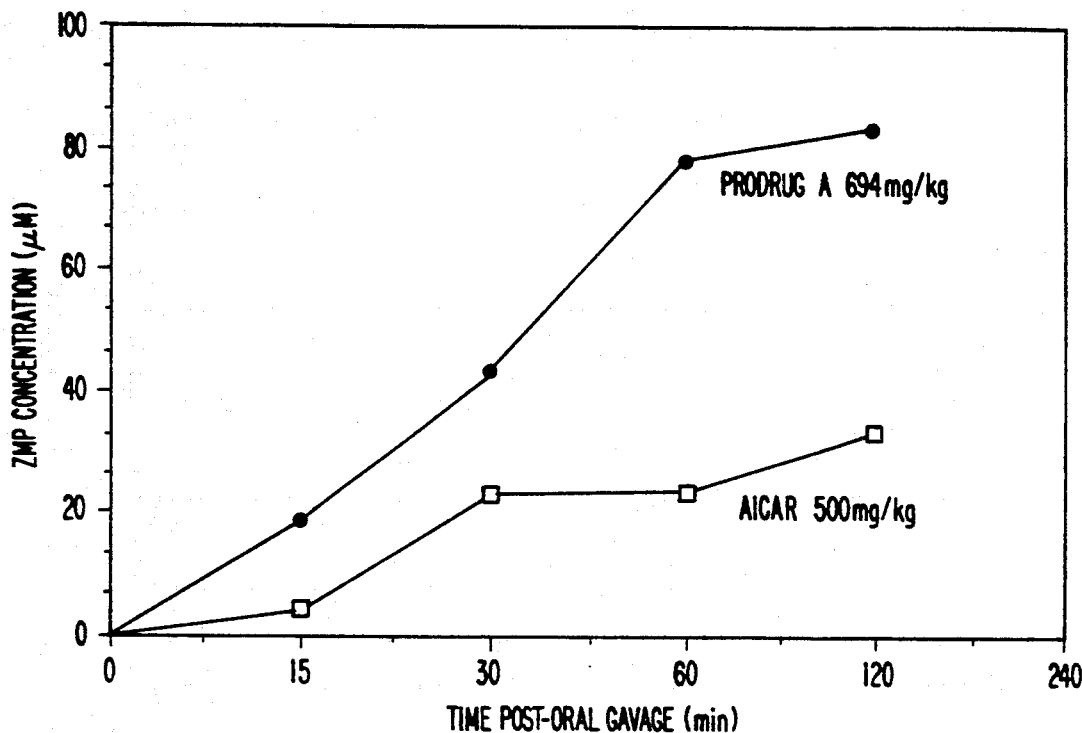
FIG. 3 depicts the effects of oral administration of AICA riboside and Prodrug A on ZMP concentration in rat heat tissue.

A comparison of adenosine production induced by saline, AICA riboside and Prodrug A (Compound 1 of Table I) is shown in FIG. 2. The fall in ZMP and quantitatively equivalent rise in AICA riboside level is shown in FIG. 3. The enhancement of adenosine production by Prodrug A as compared with an equimolar dose of AICA riboside without a corresponding high AICA-riboside level is tabulated in Table IV.

EXAMPLE C

Activity in Protection Against Ischemic Injury in Skin Flap

Compounds were tested for their activity in protecting against ischemic injury in a skin flap model in rats.

Animals were pretreated with AICA riboside or AICA riboside plus adenosine deaminase (ADA) 45 minutes before surgery or, as a positive control, superoxide dismutase (SOD) was used at the time of surgery. A skin flap was raised on the abdomen of a rat for 6 hours and then sewn down. The percent viability of the flaps was evaluated at days post-surgery.

Results are tabulated in Table V.

Animals treated with AICA riboside showed an increase in skin flap viability (compared with controls) which was satisticaly significant according to the Fisher Exact Test ($p < 0.05$). This effect was not as pronounced in the presence of ADA, supporting the importance of adenosine's protective role in this setting.

EXAMPLE D

Enhancement of Adenosine Release by Lymphoblasts

Prodrug compounds of the present invention and AICA riboside were tested for their activity in increasing adenosine release in cell culture.

With regard to the enhanced in vitro release of adenosine, a human splenic lymphoblast cell line (WI-L2) was used to demonstrate the effect of AICA riboside and prodrugs of the present invention on adenosine release. The history and properties of the cell line have been described by Hershfield et al. in *Science*, Vol. 197, p. 1284, 1977. The cell line was maintained in RPMI 1640 cell culture media supplemented with 20% fetal calf serum and 2 mM glutamine and equimolar concentrations of prodrug or AICA riboside and grown for 36 hours in an atmosphere of 5% carbon dioxide in air. Fetal calf serum contains purines and purine metabolizing enzymes; however, and to establish the effect of AICA riboside or prodrug during 2-deoxyglucose exposure, the WI-L2 cells were incubated in RPMI 1640 glucose-deficient medium supplemented with 10% heat-inactivated, dialyzed fetal bovine serum, 2 mM glutamine, and 1 $\mu$M deoxycoformycin.

Catabolism of cellular ATP stores was stimulated by adding 2-deoxyglucose. At sixty minutes, the amount of adenosine released by the cells into the supernatant was determined by mixing 30 microliters of chilled 4.4N perchloric acid with 300 microliters of supernatant and centrifuging the mixtures at $500 \times G$ for 10 minutes at 4° C. Each resulting supernatant was neutralized with 660 microliters of a solution containing 2.4 grams of tri-n-octylamine (Alamine 336) (General Mills) in 12.5 milliliters of 1,1,2-trichloro-1,2,2-triflouroethane (Freon-113) solvent as described by Khym in *Clinical Chemistry*, Vol. 21, p. 1245, 1975. Following centrifugation at $1500 \times G$ for 3 minutes at 4° C., the aqueous phase is removed and frozen at $-20°$ C. until assayed for adenosine and inosine. Adenosine was evaluated isocratically on a C-18 microBondapak reverse phase column equilibrated with 4 millimolar potassium phosphate, pH 3.4:acetonitrile 60% in water (95:5 v/v) buffer. Adenosine elutes at 8-10 minutes and its identity was confirmed by its sensitivity to adenosine deaminase and by spiking with adenosine standards. Continuous monitoring was performed by absorbance at 254 and 280 nm. Peaks were quantitated by comparison with high pressure liquid chromatography analysis of suitable standards.

Figure 4:
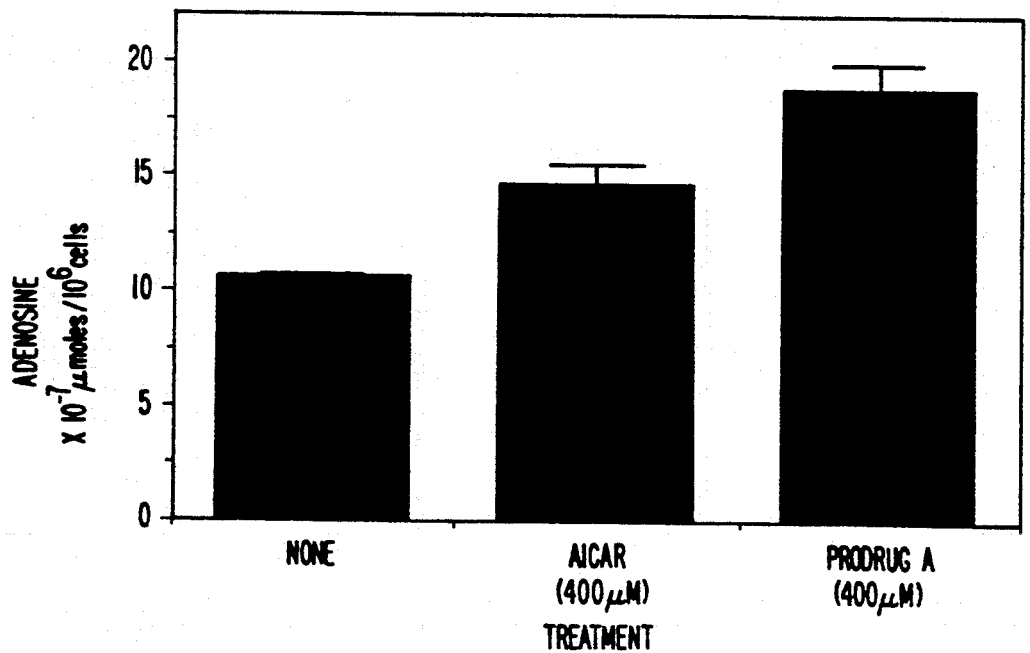
FIG. 4 depicts the effect of Prodrug A and AICA riboside on adenosine release in cell culture.

FIG. 4 shows the effect of 36 hour pretreatment with AICA riboside or Prodrug A on enhancement of adenosine release from lymphoblasts.

EXAMPLE E

Enhanced Oral Bioavailability

AICA riboside was administered to Sprague-Dawley rats at a dose of 250 mg/kg or 500 mg/kg, prodrug compounds of the present invention were administered at an equal molar dose.

At 15, 30, 60 and 120 minutes after gavage, the animals were sacrificed. The tissues were obtained and frozen immediately for nucleoside and nucleotide analysis. The tissue samples obtained were liver, heart, brain and whole blood. After initial freezing in liquid nitrogen, the tissue samples were extracted with trichloroacetic acid and neutralized with alamine freon. The tissue samples were evaluated by HPLC on a Whatman Partsil-10 (SAX) column for nucleosides and bases as described in Example 6.

In two separate experiments, at a dose equimolar to the dose of AICA riboside used, 3'-isobutoxycarbonyl AICA riboside ("Prodrug A") exhibited increased oral bioavailability as evidenced by an increase in ZMP levels in liver, whole blood and heart. Tests wer run with 8 rats.

Figure 5A:
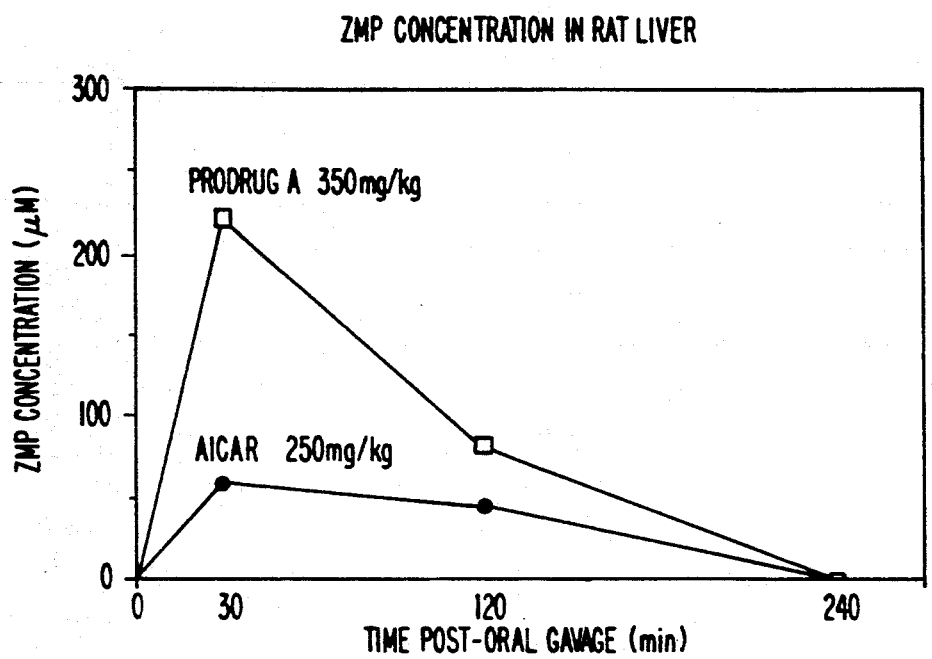
FIG. 5(a) and (b) depict the effects of oral administration of AICA riboside and Prodrug A on ZMP concentration in rat liver.
Figure 5B:
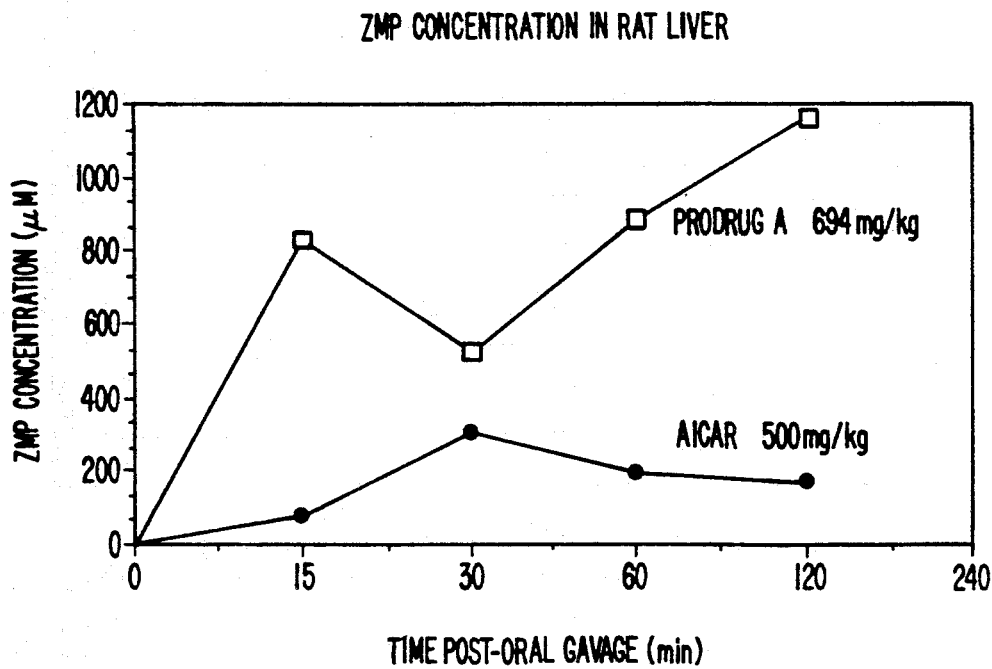

FIGS. 5(a) and (b) show ZMP concentrations in rat liver at doses of a molar equivalent of 250 mg/kg and 500 mg/kg AICA riboside.

TABLE I

Compounds of the formula:

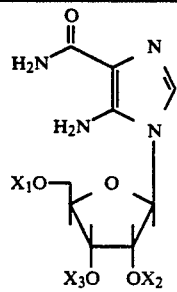

| Compound | $X_1$ | $X_2$ | $X_3$ |
|---|---|---|---|
| 1 | —H | —H | —COCH$_2$CH(CH$_3$)$_2$ |
| 2 | —COCH$_2$CH(CH$_3$)$_2$ | —COCH$_2$CH(CH$_3$)$_2$ | —H |
| 3 | —COCH$_2$CH$_3$ | —H | —H |
| 4 | —COCH$_2$CH$_2$CH$_3$ | —H | —H |
| 5 | —COCH$_2$CH$_2$CH$_3$ | —COCH$_2$CH$_2$CH$_3$ | —H |
| 6 | —CO—(CH$_2$)$_5$CH$_3$ | —H | —H |
| 7 | —CCH$_3$ | —H | —H |
| 8 | —H | —CCH$_3$ | —CCH$_3$ |
| 9 | —H | —CCH$_3$ | —H |
| 10 | —CCH(CH$_3$)$_2$ | —H | —H |
| 11 | —CC(CH$_3$)$_3$ | —H | —H |
| Cl | —CCH$_3$ | —CCH$_3$ | —CCH$_3$ |

TABLE II
Compounds of the formula:
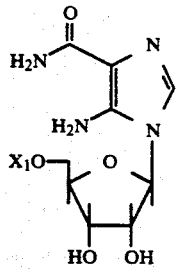
| Compound | $X_1$ |
|---|---|
| 12 | 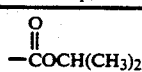 —COCH(CH$_3$)$_2$ |
| 13 |  —COC(CH$_3$)$_3$ |
| 14 | 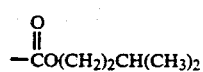 —CO(CH$_2$)$_2$CH(CH$_3$)$_2$ |
| 15 | 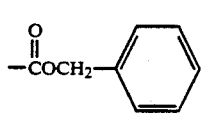 —COCH$_2$—C$_6$H$_5$ |
| 16 |  —CCH$_2$CH(CH$_3$)$_2$ |
TABLE II-continued
Compounds of the formula:
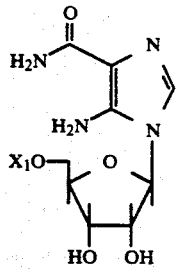
| Compound | $X_1$ |
|---|---|
| 17 | 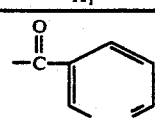 |
| 18 | 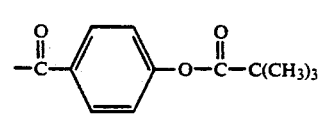 |
| 19 | 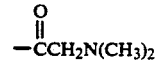 —CCH$_2$N(CH$_3$)$_2$ |
| 20 | 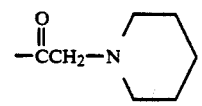 |
TABLE III
Compounds of the formula
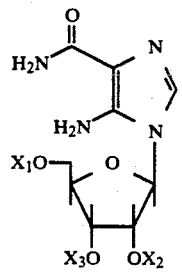
| Compound | $X_1$ | $X_2$ | $X_3$ |
|---|---|---|---|
| 21 | 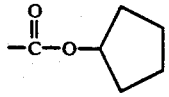 | —H | —H |
| 22 | —H | —H | 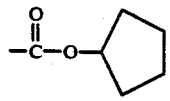 |
| 23 | 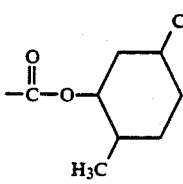 | —H | —H |

TABLE III-continued

Compounds of the formula

[Structure: ribose with X1O-CH2, X3O, OX2, N-glycoside to imidazole bearing C(=O)NH2 and NH2 groups]

| Compound | X1 | X2 | X3 |
|---|---|---|---|
| 24 | —H | —H | —C(=O)O-cyclohexyl with CH(CH3)2 and H3C substituents (menthyl ester) |
| 25 | —C(=O)O-cyclopropyl | —H | —H |
| 26 | —H | —H | —C(=O)O-cyclopropyl |
| 27 | —C(=O)CH2CH2OCH3 | —H | —H |
| 28 | —H | —H | —C(=O)—O—CH2CH2OCH3 |
| 29 | —C(=O)CH2CH2—O—phenyl | —H | —H |
| 30 | —H | —H | —C(=O)CH2CH2O—phenyl |
| 31 | —C(=O)O-(γ-butyrolactone) | —H | —H |
| 32 | —H | —H | —C(=O)O-(γ-butyrolactone) |

TABLE IV

| | Tissue Concentration (nMoles/g) | | |
|---|---|---|---|
| Treatment | Adenosine | AICA Riboside | ZMP |
| Control (Saline) | 272 ± 31 | 0 | 0 |
| AICA-riboside | 409 ± 60 | 774 ± 73 | 385 ± 15 |
| Prodrug A | 553 ± 46 | 592 ± 55 | 161 ± 9 |

TABLE V

Protection against Ischemic Injury in Skin Flap

| Treatment | Number Evaluated | % Viable |
|---|---|---|
| Control | 24 | 33 |
| AICA riboside | 8 | 75 |
| AICA riboside + ADA | 7 | 43 |

TABLE V-continued

| Protection against Ischemic Injury in Skin Flap | | |
|---|---|---|
| Treatment | Number Evaluated | % Viable |
| SOD | 18 | 68 |

We claim:

1. A method for enhancing the extracellular concentration of adenosine around cells having a decreased ratio of synthesis of adenosine triphosphate to breakdown of adenosine triphosphate due to a pathologic process comprising the aministration of an 5-amino-4-imidazolecarboxamine riboside prodrug which comprises a modified 5-amino-4-imidozolecarboxomide riboside having an 5-amino-4-imidazolecarboxamide ribosyl moeity and at least one hydrocarbyloxycarbonyl or hydrocarbylcarbonyl moiety per equivalent weight of 5-amino-4-imidazolecarboxamide ribosyl moiety.

2. The method according to claim 1 wherein said pathologic process is a seizure.

3. The method according to claim 1 wherein said pathologic process is a stroke.

4. The method according to claim 1 wherein said pathologic process isd coronary ischemia.

5. The method according to claim 1 wherein said prodrug which enhances the cellular synthesis and release of adenosine is administered as a prolylactic.

6. The method of claim 5 wherein said pathologic process is a stroke.

7. The method of claim 5 wherein said pathologic process is a heart attack.

8. The method of claim 5 wherein said pathologic process is angina pectoris.

9. The method according to claim 1 wherein said prodrug comprises a compound of the formula:

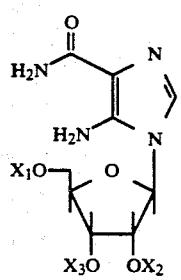

wherein $X_1$, $X_2$ and $X_3$ are independently hydrogen,

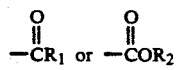

wherein $R_1$ and $R_2$ are independently hydrocarbyl, or two of $X_1$, $X_2$ and $X_x$ taken together from a cyclic carbonate group.

10. The method according to claim 9 wherein $X_1$, $X_2$ and $X_3$ are acetyl.

11. The method according to claim 9 wherein one or two of $X_1$, $X_2$ and $X_3$ is

12. The method according to claim 11 wherein one of $X_1$, $X_2$ is

13. The method according to claim 12 wherein $X_1$ is isobutyryl and $X_2$ and $X_3$ are hydrogen.

14. The method according to claim 12 wherein $X_1$ is pivalyl and $X_2$ and $X_3$ are hydrogen.

15. The method according to claim 12 wherein $X_1$ is isovaleryl and $X_2$ and $X_3$ are hydrogen.

16. The method of claim 9 wherein said prodrug which enhances the cellular synthesis and release of adenosine is administered as a proplylactic.

17. The method according to claim 16 wherein said pathologic process is a stroke.

18. The method according to claim 16 wherein said pathologic process is a heart attack.

19. The method according to claim 16 wherein said pathologic process is angina pectoris.

20. The method according to claim 16 wherein $X_2$ is hydrogen, and one of $X_1$ and $X_3$ is hydrogen and the other is

21. The method according to claim 20 wherein $R_2$ is lower alkyl of from 1 to about 6 carbon atoms having a secondary carbon atom.

22. A method of treating patients having chronic low adenosine levels or who would benefit from increased central nervous system adenosine levels comprising the administration of an 5-amino-4-imidazolecarboxamide riboside prodrug which comprises a modified 5-amino-4-imidazolecarboxamide having an 5-amino-4-imidazolecarboxamide ribosyl moiety and at least one hydrocarbyloxycarbonyl or hydrocarbylcarbonyl moiety per equivalent weight of 5-amino-4-imidazolecarboxamide ribosyl moiety.

23. The method according to claim 22 wherein said prodrug comprises a compound of the formula:

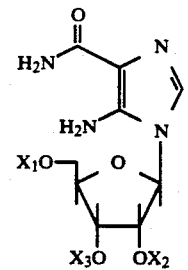

wherein $X_1$, $X_2$ and $X_3$ are independently hydrogen,

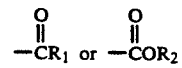

wherein $R_1$ and $R_2$ are independently hydrocarbyl, or two of $X_1$, $X_2$ and $X_3$ taken together from a cyclic carbonate group.

24. The method according to claim 23 wherein $X_2$ is hydrogen and one of $X_1$ and $X_2$ is hydrogen and the other is

25. The method according to claim 24 wherein $R_2$ is lower alkyl of from 1 to about 6 carbon atoms having a secondary carbon.

26. A method of inhibiting homocysteine induced seizures in an animal which comprises administering to said animal a therapeutically effective amount of 5-amino-4-imidazolecarboxamide riboside or an 5-amino-4-imidazolecarboxamide riboside prodrug which comprises a modified 5-amino-4-imidazolecarboxamide riboside having an 5-amino-4-imidazolecarboxamide ribosyl moiety and at least one hydroarbyloxycarbonyl or hydrocarbylcarbonyl moiety per equivalent weight of 5-amino-4-imidazolecarboxamide ribosyl moiety sufficient to increase the synthesis and release of extracellular adenosine.

* * * * *

UNITED STATES PATENT AND TRADEMARK OFFICE
CERTIFICATE OF CORRECTION

PATENT NO. : 5,082,829                                  Page 1 of 2

DATED     : January 21, 1992

INVENTOR(S) : Gruber, Harry E.; Browne, Clinton E.; vgarkar, Bheemaro G.; reich, Jack W.

It is certified that error appears in the above-identified patent and that said Letters Patent is hereby corrected as shown below:

```
Column 1, Line 65:  [since] Since
Column 2, Line 60:  [9enerally] generally
Column 4, Line 24:  [ove] over,
          Line 39:  [ca] can
Column 12, Line 39: [treatmen] treatment Column 16, Line 24: [indicaated] indicated
Column 16, Line 40: [1 to and in] 1 to 4 and in Column 18, Line 33: [2 mM] 2mM
```

UNITED STATES PATENT AND TRADEMARK OFFICE
CERTIFICATE OF CORRECTION

PATENT NO. : 5,082,829                    Page 2 of 2
DATED     : January 21, 1992
INVENTOR(S) : Gruber, Harry E.; Browne, Clinton E.; vgarkar, Bheemaro G.; reich, Jack W.

It is certified that error appears in the above-indentified patent and that said Letters Patent is hereby corrected as shown below:

```
Claim 1,  Line 13, Column 25: [aministration] administration
Claim 4,  Line 25, Column 25: [isd] is
Claim 5,  Line 28, Column 25: [prolylactic] prophylactic
Claim 16, Line 14, Column 26: [proplylactic] prophylactic
```

Signed and Sealed this

Twenty-fifth Day of April, 1995

Attest:

BRUCE LEHMAN

*Attesting Officer*        *Commissioner of Patents and Trademarks*